United States Patent [19]

McCormick et al.

[11] Patent Number: 5,104,975

[45] Date of Patent: * Apr. 14, 1992

[54] COMPOSITIONS FOR DETECTING RAS GENE PROTEINS AND CANCER THERAPEUTICS

[75] Inventors: Francis P. McCormick, Albany; Kirston E. Koths, El Cerrito; Robert F. Halenbeck, San Rafael; Mary M. Trahey, Oakland, all of Calif.

[73] Assignee: Cetus Corporation, Emeryville, Calif.

[*] Notice: The portion of the term of this patent subsequent to Jul. 3, 2004 has been disclaimed.

[21] Appl. No.: 216,888

[22] Filed: Jul. 8, 1988

[51] Int. Cl.$^5$ .................. C07K 3/22; C07K 15/00; C07K 15/06

[52] U.S. Cl. .................. 530/350; 530/395; 530/413; 530/416; 530/828

[58] Field of Search ............... 530/350, 828, 413, 395, 530/416, 417

[56] References Cited

U.S. PATENT DOCUMENTS 4,404,188 9/1983 Donahoe et al. .................. 424/105

OTHER PUBLICATIONS

Cales et al, Nature (England), 332(6164) pp. 548-551, Apr. 7, 1988, "The Cytoplasmic Protein Gap is Implicated as the Target for Regulation by the Ras Gene Product".
Jackson B. Gibbs, et al., 1988, PNAS (U.S.A.), 85:5026-5030.
McCormick, et al., 1988, Cold Spring Harbor Symposia on Quantitative Biology, LIII:849-854, Cold Spring Harbor Laboratory.
Adari, H., et al., 1988, Science, 240: 518-521.
Sigal, Irving S., 1988, Nature, 332:485-486.
McCormick, F., et al., 1988 CSH, (Abstract Only).
Trahey, M., et al., (Abstract Only).

Primary Examiner—Christine Nucker
Assistant Examiner—Laurie A. Scheiner
Attorney, Agent, or Firm—Gregory J. Giotta; Albert P. Halluin

[57] ABSTRACT

Compositions useful for detecting ras gene proteins are described consisting of GTP and a protein having an apparent reduced molecular weight of about 115,000–120,000 daltons, or fragments derived therefrom, that stimulate ras protein guanosine triphosphatase activity. Also described are methods whereby the compositions are used to identify cancer therapeutics.

18 Claims, 2 Drawing Sheets

REDUCED 10% SDS PAGE
(COOMASSIE-STAINED)

COMPOSITIONS FOR DETECTING RAS GENE PROTEINS AND CANCER THERAPEUTICS

FIELD OF THE INVENTION

This invention relates generally to the field of oncology, and particularly to diagnostic compositions useful in testing for cancer. Additionally, the invention concerns compositions that can be employed both as cancer diagnostics, as well as in a scheme for identifying cancer therapeutics.

BACKGROUND OF THE INVENTION

Several genes have been identified that are thought to play a role in regulating normal cell growth. A subset of these genes, termed ras, consists of at least three members, N-ras, H-ras, and K-ras2. Altered forms of ras, termed oncogenes, have been implicated as causative agent in cancer. Both the normal cellular genes, and the oncogenes encode chemically related proteins, generically referred to as p21.

Ras oncogenes, and their normal cellular counterparts, have been cloned and sequenced from a variety of species. Comparison of the structure of these two genes has revealed that they differ by point mutations that alter the amino acid sequence of the p21 protein. Naturally occurring mutations in the ras oncogenes have been identified in codons 12, 13, 59, and 61. In vitro mutagenesis work has shown that mutations in codon 63, 116, and 119 also result in transforming activity. The most frequently observed mutation which converts a normal cellular ras gene into its oncogenic counterpart is a substitution of glycine at position 12 by any other amino acid residue, with the exception of proline. Transforming activity is also observed if glycine is deleted, or if amino acids are inserted between alanine at position 11 and glycine at position 12.

Mutations at position 61 also play an important role in the generation of ras oncogenes. Substitution of glutamine for any other amino acid, except proline or glutamic acid in the cellular ras gene yields ras oncogenes with transforming activity.

In relation to normal cellular ras genes and their oncogenic counterparts, there are at least four known retroviral ras oncogenes which exhibit transforming activity. Unlike their non-retroviral analogues, the retroviral genes exhibit two mutations. The biologically significance of these double mutations is at present unclear.

Both the normal ras and oncogenic p21 proteins, regardless of their phylogenetic origin, bind guanine nucleotides, GTP and GDP, and possess intrinsic GTPase activity. Temeles et al., *Nature*, 313:700 (1985). The significance of these biochemical properties to the biological activities of the ras proteins has been demonstrated as follows: first, microinjection of anti-ras antibodies that interfere with guanine nucleotide binding reverses the malignant phenotype of NIH 3T3 cells transformed by ras oncogenes. Clark, et al., *Proc. Natl. Acad. Sci. U.S.A.*, 82:5280 (1985); Feramisco, et al., *Nature*, 314:639 (1985). Second, ras oncogenic proteins that exhibit mutations which result in the inability of p21 to bind guanine nucleotides do not transform NIH 3T3 cells. Willumsen, et al., *Mol. Cell. Biol.*, 6:2646 (1986). Third, some ras oncogenes produce p21 proteins that have much reduced GTPase activity compared to their normal cellular counterparts. The biological role of GTPase activity associated with either ras or its oncogenic counterpart remains unknown.

Recently a cytoplasmic factor has been identified which stimulates normal ras p21 GTPase activity, but does not effect GTPase activity associated with the oncogenic mutants. M. Trahey and F. McCormick, *Science*, 238:542 (1987). The activity has been associated with a protein, termed GAP, which is the acronym for GTPase activating protein. GAP is thought to be a cytoplasmic protein but is presumably capable of moving from the cytosol to the plasma membrane where it interacts with p21.

As alluded to above, ras oncogenes have been implicated in the development of a variety of tumors, and have been shown to be involved in about 10-40% of the most common forms of human cancer. H. Varmus, *Annual Rev. Genetics*, 18:553 (1984); M. Barbacid, in *Important Advances in Oncology* (1986), ed. B. DeVita, S. Helman, S. Rosenberg, pages 3-22, Philadelphia:Lippincott. For example, ras oncogenes have been consistently identified in carcinomas of the bladder, colon, kidney, liver, lung, ovary, pancreas and stomach. They also have been identified in hematopoietic tumors of lymphoid and myeloid lineage, as well as in tumors of mesenchymal origin. Furthermore, melanomas, teratocarcinomas, neuroblastomas, and gliomas have also been shown to possess ras oncogenes.

Considering the possible association of ras oncogenes and cancer, there has been considerable work focused on diagnostic tests for detecting the presence of the oncogene product, p21, or the mutant oncogenes. Early tests, which are still employed in many instances, identify the presence of ras oncogenes in transfection assays which identify p21 by its ability to transform NIH 3T3 cells. Lane, et al., *Proc. Natl. Acad. Sci. U.S.A.*, 78:5185 (1981); and B. Shilo, and R. A. Weinberg, *Nature*, 289:607 (1981). This method is insensitive, laborious, and requires a skilled laboratory technician to perform adequately.

A second diagnostic method centers around oligonucleotide probes to identify single, point mutations in genomic DNA. This technique is based on the observation that hybrids between oligonucleotides form a perfect match with genomic sequences, that is, non-mutated genomic sequences are more stable than those that contain a single mismatch. The latter, of course, being a point mutation in p21 associated with the ras oncogenes. Although this technique is clearly more sensitive and easier to perform than the transfection assay, it is nevertheless also cumbersome to perform. This is because there are theoretically almost 100 base substitutions which can yield ras oncogenes. Thus, in order to be able to detect these substitutions multiple oligonucleotide probes must be employed containing each of the three possible substitutions at a particular residue. Bos, et al., *Nature*, 315:726 (1985); Valenzuela, et al., *Nuc. Acid Res.*, 14:843 (1986).

In addition to the transfection and oligonucleotide assays, additional nucleic acid hybridization techniques have been developed to identify ras oncogenes. One such method is based on the unusual electrophoretic migration of DNA heteroduplexes containing single based mismatches in denaturing gradient gels. Myers et al., *Nature*, 313:495 (1985). This technique only detects between about 25-40% of all possible base substitutions, and requires a skilled technician to prepare the denaturing gradient gels. More sensitive techniques which are refinements of this technique are described by Winter, et al., *Proc. Natl. Acad. Sci. U.S.A.*, 82:7575 (1985); and Myers, et al., *Science*, 230:1242 (1985).

Immunologic approaches have been taken to detect the product of the ras oncogenes. Antibodies, either polyclonal or monoclonal, have been generated against the intact ras oncogene p21, or against chemically synthesized peptides having sequences similar to oncogene p21, or the non-transforming counterpart. U.S. patent application Ser. No. 938,581; EP Patent Publication 108,564 to Cline et al.; Tamura, et al., *Cell*, 34:587 (1983); PCT Application WO/84/01389 to Weinberg et al. For the most part, unfortunately, antibodies have been disappointing as diagnostic tools with which to identify ras oncogenic p21 in human tissue sections. This is because either the antibodies that have been generated to date recognize the normal cellular ras protein as well as the oncogenic protein, or in those instances where a monoclonal antibody has been generated that specifically recognizes the oncogenic protein, it exhibits non-specific staining of tumor biopsies.

While ras oncogenic p21 is an effective tumorigenic agent, recent studies have shown that normal ras p21 can induce the malignant phenotype. Chang et al., *Nature*, 297:7479 (1982); Pulciani, et al., *Mol. Cell. Biol.*, 5:2836 (1985). For example, transfection of normal H-ras DNA has been shown to induce malignant transformation. It is further noteworthy that normal ras gene amplification has been observed in several human tumors, and has an apparent incidence of about 1%. Pulciani, et al., above; Yokota, et al., *Science*, 231:261 (1986). The various diagnostic test used to detect ras oncogenes or oncogenic p21 have been applied to the detection of normal ras p21 with similar limited success.

It should be apparent from the foregoing that while there are a number of diagnostic methods for determining the presence of ras oncogenes, or their transforming proteins, there is still a need for fast and reliable diagnostic methods that will permit their routine identification.

By and large, the vast majority of cancer therapeutics function by killing dividing cells, and because of this lack of specificity, kill normal as well as cancer cells. Thus, despite knowledge of the existence of normal cellular ras genes, or their oncogenic counterparts, there have been identified few therapeutics that can interfere with, or reverse the transformed state that are not generally cytotoxic. Valeriote, F. and Putten, L., *Cancer Res.*, 35:2619 (1975). The exceptions include anti-ras monoclonal antibody, Y13-259, which has been shown to selectively block the morphologic transformation induced by oncogenic ras proteins. Mulcahy, et al., *Nature*, 313:241 (1985). Also, U.S. patent application Ser. No. 938,581 shows a monoclonal antibody directed against oncogenic p21 having serine at position 12. This antibody, when microinjected into ras transformed cells causes the cells to revert to a normal cell phenotype. It has no effect on normal cells. Unfortunately, because ras is located on the cytoplasmic side of the plasma membrane, where it interacts with GTP and GAP, large molecular weight molecules such as antibodies may not have immediate therapeutic significance in the clinical setting. Thus, a method that will facilitate the identification of cancer therapeutics is sorely needed.

SUMMARY OF THE INVENTION

In accordance with the present invention, compositions are described that are useful both as diagnostics for cancers arising from the expression of normal cellular or oncogenic ras genes, and in the clinical setting to identify anti-cancer therapeutics effective against such cancers.

A second aspect of the invention relates to compositions consisting of defined concentrations of normal cellular or oncogenic ras p21, GAP (or active fragments derived therefrom), and GTP that are useful in cancer diagnosis and in clinical tests to identify anti-cancer therapeutics.

A third aspect of the invention consists of methods for purifying GAP, both the intact molecule, and biologically active fragments derived therefrom.

A further aspect of the invention is to identify structural regions of GAP, or fragments derived therefrom, that facilitate use of the molecule in a cancer diagnostic test, or in clinical tests to identify anti-cancer therapeutics.

A yet further aspect of the invention is a method for curing cancer, whereby anti-cancer therapeutics are identified by their ability to interfere with GAP binding to a complex consisting of normal or oncogenic ras p21 protein, and GTP; and formulating and administering the therapeutics to patients.

DETAILED DESCRIPTION OF THE INVENTION

Figures 1A, 1B:
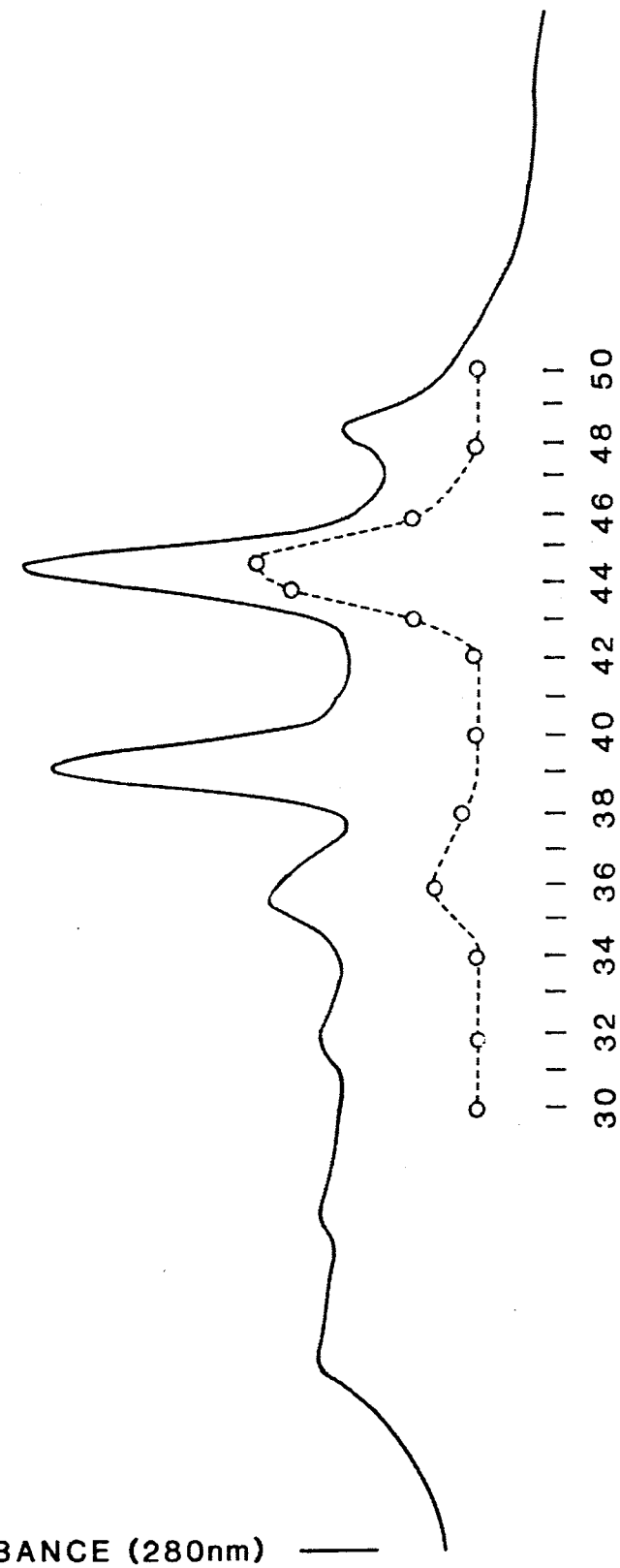
FIG. 1A shows the TSK phenyl column elution profile and FIG. 1B silver staining of SDS PAGE fractions thereof.

A better understanding of the invention described herein will be realized by providing a brief description of some of the materials and methods used in the invention.

The normal cellular ras gene, and its oncogenic counterparts are defined as described by Barbacid, N., *Ann. Rev. Biochem.*, 56:779 (1987). Similarly, the proteins encoded by these genes are also defined as described by Barbacid. Moreover, it will be appreciated that fragments of normal cellular p21 that bind GTP, and exhibit GAP stimulated GTPase activity are intended to come within the definition of ras p21.

GAP is the acronym for guanine triphosphatase activating protein, and is defined as a protein having a molecular weight and amino acid sequence as described herein, and that has the further properties of stimulating GTPase activity of normal cellular ras p21, while having little or no stimulatory activity when combined with oncogenic ras p21 proteins and GTP. Of course, it will be understood by those skilled in the art that GAP may also exist as aggregates or multimers under certain conditions, and these forms are intended to come within the scope of the definition. Moreover, the definition is further intended to cover fragments of GAP that exhibit activity. Exemplary of such a fragment is a molecule having a reduced subunit molecular weight of about 50,000-60,000 as shown herein.

It will further be appreciated with regard to the chemical structure of GAP, that its precise structure may depend on a number of factors. As all proteins contain ionizable amino and carboxyl groups it is, of course, apparent that GAP may be obtained in acid or basic salt form, or in neutral form. It is further apparent, that the primary amino acid sequence may be augmented by derivatization using sugar molecules (glycosylation) or by other chemical derivatizations involving covalent or ionic attachment to GAP with, for example, lipids, phosphate, acetyl groups and the like, often occurring through association with saccharides. These modifications may occur in vitro or in vivo, the latter being performed by a host cell through post translational processing systems. It will be understood that such modifications, regardless of how they occur, are intended to come within the definition of GAP so long as the activity of the protein, as defined herein, is not significantly reduced. It is to be further expected, of course, that such modifications to GAP may quantitatively or qualitatively increase or decrease the biological activity of the molecule, and such chemical modifications are also intended to come within the scope of the definition of GAP.

As used herein, "chromatography" is defined to include application of a solution containing a mixture of compounds to an adsorbent, or other support material which is eluted, usually with a gradient or other sequential eluant. Material eluted from the support matrix is designated eluate. The sequential elution is most routinely performed by isolating the support matrix in a column and passing the eluting solution(s), which changes affinity for the support matrix, either stepwise or preferably by a gradient. It will be appreciated that encompassed within the definition "chromatography" is positioning the support matrix in a filter and sequentially administering eluant through the filter, or in batch-mode applications.

The phrase "hydrophobic interaction matrix" is defined to mean an adsorbent that is a hydrophobic solid such as polystyrene resin beads, rubber, silica-coated silica gel, or crosslinked agarose sufficiently substituted with hydrophobic functional groups to render the material hydrophobic. Alkyl substituted agarose and aryl substituted agarose such as, for example, phenyl or octyl agarose are representative hydrophobic materials. Mixtures of materials that are chromatographically separated on a hydrophobic interaction chromatography matrix are generally first adsorbed to the matrix in a high salt solution, and subsequently desorbed from the matrix by elution in a low salt solution, or a hydrophobic solvent such as a polyol.

"Anion exchange matrix" is defined to mean a solid or gel support matrix that is charged in aqueous solutions. The support matrix may be agarose sufficiently substituted with amine functional groups to have a net charge in aqueous solutions. The material to be adsorbed is generally bound to the anion exchange matrix in a low salt solution and is generally eluted from the anion exchange matrix in a high salt eluant containing anions such as chloride ion which bind to the anion exchange matrix and displace the adsorbed material.

By the phrase "high salt concentration conditions" is meant an aqueous solution wherein an ionic substance is present to create conditions of high ionic strength. Ionic strength is defined as is generally understood in the art and can be calculated from the putative concentrations of the various ions placed in solution modified by their activity coefficient. High salt concentrations that are routinely employed are typified by solutions containing high concentrations of ammonium sulfate; however, other salts, such as sodium chloride, potassium chloride, sodium sulfate, sodium nitrate, or sodium phosphate may also be employed.

The definition of "affinity chromatography" is understood to be similar to that of Wilchek, et al., *Methods in Enzymology*, 104:3 (1984). In its broadest intended definition, "affinity chromatography" is a "method of purification based on biological recognition". Briefly, the procedure involves coupling a ligand to a solid support, and contacting the ligand with a solution containing therein a ligand recognition molecule which binds to the ligand. Subsequently, the ligand recognition molecule is released from the ligand and isolated in pure form. It will be understood that a variety of ligands can be employed in affinity chromatography as discussed by Wilchek, et al., and examples of these include lectins, antibodies, receptor-binding proteins and amino acids.

GENERAL DESCRIPTION

The instant invention provides a description of compositions and methods of using the same for diagnosing cancer, and for identifying cancer therapeutics. The main components of the compositions are ras p21 protein, either the normal cellular protein or the oncogenic mutants, guanosine triphosphate, or other hydrolyzable guanine nucleotide, and GAP. There are additional reagents present in the compositions, but these are ancillary to the three main components. Each of the three main components will now be discussed separately.

GAP Purification

Guanosine triphosphatase activating protein, or GAP, is widely expressed in higher eukaryotes. GAP has been detected in cell extracts from human and mouse normal tissues including brain, liver, placenta, B cells, and platelets. It has additionally been found in non-transformed cell cultures including NIH 3T3, as well as transformed cell lines, including human mammary cancer cells (MCF-7), retinoblastoma cells (Y79), and Wilm's tumor (G401). GAP is also present in insect cells such as, for example, *Spodoptera fragipedra*. From many of these cells or tissues, GAP may be isolated, albeit with minor variations in the purification protocols and the like.

The general scheme for GAP isolation and purification consist of releasing the molecule from the cytoplasm of appropriate cells, tissues or organs, followed by removing insoluble material and subjecting the soluble GAP fraction to cation exchange chromatography, followed by a second chromatographic step wherein the eluant from the cation exchanger is passed over an anion exchanger. GAP is eluted from the anion exchanger, and further purified by subjecting it to a third chromatographic step, either hydrophobic chromatography, or a second cation exchange step.

More specifically, GAP is prepared by releasing the molecule from the cytosol using any number of techniques including freeze thawing, sonication, mild detergent extraction, etc. This procedure is preferably carried out in a physiologically buffered solution containing one or more protease inhibitors. Moreover, to further inhibit protease activity, especially those proteases that rely on metal ions for activation, the extraction solution may contain metal ion chelators. The preferred extraction solution is a physiologically balanced salt solution containing the chelators ethyleneglycoltrichloroacetic acid (EGTA), or ethylenediaminetrichloroacetic acid (EDTA), plus the protease inhibitor phenylmethylsulfonylfluoride (PMSF). The metal ion chelator(s), as well as the protease inhibitor(s) are present at concentrations that effectively inhibit proteolysis, preferably about 5 mM and 100 μM, respectively. However, it will, of course, be appreciated by those skilled in the art that since the types and amounts of proteases vary depending on the starting material used to extract GAP, that the concentrations that the protease inhibitors or chelators are used at, if indeed used at all, will also vary.

The mixture containing GAP is clarified by centrifugation, or in other ways to remove insoluble material from the aqueous cytosol fraction. If the cytosol fraction contains low amounts of GAP it can be concentrated by any one of several techniques well known to those skilled in the art, including high salt precipitation, such as for example with ammonium sulfate, or by ultra filtration. If GAP is concentrated by precipitation, it is preferably subsequently resuspended in a suitable physiologically balanced salt solution containing protease inhibitor(s) and preferably about 0.1% of a nonionic detergent, such as NP40. This solution is then prepared for ion exchange chromatography by dialyzing it against a compatibly buffered chromatographic solution, preferably containing millimolar phosphate, a metal ion chelator, a reducing agent, and a protease inhibitor. Additionally, because GAP activity is stimulated by the presence of divalent cations such as magnesium chloride, it may also be present in the solution. The pH of the solution is preferably about 6.0.

The GAP dialyzate is then subjected to chromatographic purification consisting preferably of three steps. The first involves purification using an ion exchange chromatographic step compatible with the GAP extraction buffer. Since the preferred extraction buffer contains phosphate, the initial step is purification of GAP by cation exchange chromatography. The second consists of ion exchange chromatography wherein the ion exchange matrix has the opposite ion binding capacity from that of the first ion exchanger employed.

Thus, the preferred purification scheme will consist of applying the phosphate solution containing GAP to a cation exchanger, and eluting GAP therefrom, preferably using solutions which alter the pH or conductivity of the solution. More preferably GAP will be eluted by applying either a gradient or non-gradient salt solution, and most preferably will be eluted using a linear gradient of sodium chloride over the range of about 0–0.6 molar.

The preferred cation exchanger is a SP-cellulose cation exchanger. Such are commercially available from AMF Molecular Separations Division, Meridian, CT. under the brand name ZetaPrep SP cartridges. The SP-cellulose cation exchanger is an elastic 3-dimensional network composed of cellulosic backbones cross-linked with vinyl polymer containing pendant sulfopropyl functional groups. The matrix is preferably adapted for radial flow passage of the GAP solution. The flow rate of the solution through the matrix will depend upon the size and geometry of the matrix used. It will be apparent to those skilled in the art, however, that care should be taken to avoid exceeding the unit capacity of the matrix with GAP. If the capacity is exceeded, GAP will not be totally retained and excess unretained GAP will be present in the effluent. The capacity of the matrix to retain GAP can be monitored by assaying for GAP in the effluent using one of the assays described below.

Fractions containing GAP are prepared for the second chromatographic step, that is, anion exchange chromatography. This consists of combining the fractions and adjusting the solution to a pH, and ionic strength compatible with anion exchange chromatography. A variety of anion exchangers are available, and depending on the type employed, the concentrations of these reagents will vary. DEAE-Sepharose or TSK-DEAE-5-PW may be employed. The general procedures for preparing and using these matrices are known to those skilled in the art.

The preferred anion exchanger is TSK-DEAE-5-PW matrix. It is prepared by equilibrating it with a solution containing chloride ions at a pH of 8.5. More preferably, the solution will consist of Tris hydrochloride, pH 8.5 plus a reducing agent, a metal chelator, magnesium chloride, and a protease inhibitor. The concentrations of the metal chelator and protease inhibitor will vary and depend on how extensively GAP is proteolyzed, and whether the proteases responsible are activated by metal ions. The concentration of monovalent cations, such as magnesium chloride and reducing agent can be determined empirically by monitoring GAP activity. Those concentrations which maintain the highest activity will be utilized. Generally, it is preferred that magnesium chloride and the reducing agent be present in the range of about 0.5–1 mM, and 0.1–1 mM, respectively.

The solution is then passed through the anion exchange matrix whereupon GAP binds to the matrix. GAP is subsequently eluted from the matrix using solutions which alter the pH or conductivity. The preferred elution method consists of eluting GAP using a linear salt gradient ranging from 0–0.6 molar sodium chloride. The purity and activity of GAP so obtained can be monitored by the GTPase assay described below, and by sodium dodecyl sulfate polyacrylamide gel electrophoresis run under reducing conditions. Using these techniques it was determined that GAP has a molecular weight of about 115,000–120,000 daltons.

The third chromatographic step consist of applying, after the anion exchange chromatography, either a second cation exchange step, or a hydrophobic interaction chromatographic step. The most preferred purification scheme utilizes a second cation exchange step. Application of either of these methods will generally increase the purity of GAP to about 95%. If a cation exchange column is chosen, the materials and methods described above are similarly applicable here. Generally, this will consist of decreasing the salt concentration present in the anion column eluates and adjusting the pH to about 6.0. Here, as in the initial cation chromatographic step, several different types of cation exchange matrices can be employed; however, the preferred matrix is a SP-TSK column which is run under high pressure.

If hydrophobic chromatography is selected, the ionic strength of the eluate from the anion exchanger should be increased to be compatible with hydrophobic interaction chromatography. The solution can then be passed through a hydrophobic interaction chromatographic matrix, and eluted using techniques known in the art, including decreasing the salt concentration, or with a chaotropic agent. Either of the latter solutions may be used alone, or in combination.

A variety of hydrophobic interaction chromatographic matrixes may be utilized. Generally, the materials and methods for utilizing hydrophobic chromatography are described by Shaltie, S., *Methods in Enzymology*, 104:69 (1984). While it is apparent there are many hydrophobic chromatographic materials and methods that may be employed to purify GAP, phenyl Sepharose is preferred, and it is further preferred that the chromatography be employed under high pressure. The general procedures for forming high pressure liquid chromatography involving a phenyl derivatized matrix are described by Regmaer, F., *Methods in Enzymology*, 91:137 (1983). The preferred phenyl derivatized matrix is available commercially from Bio-Rad Corporation, and is sold under the trade name Biogel TSK phenyl-5-PW.

It will be additionally appreciated by those skilled in the art that an alternative purification scheme may consist of a cation and anion chromatographic exchange step, followed by an affinity chromatographic step. This may be achieved by binding GAP to one or more plant lectins having a known carbohydrate specificity compatible with carbohydrates which may be present on GAP, or by binding GAP to anti-GAP antibodies. In either event, GAP can then be released from the affinity matrix using the appropriate sugar if the matrix is composed of a lectin, or by pH or chaotropic agents if the matrix is composed of antibody.

Because GAP is a protease-sensitive molecule that is broken down into lower molecular weight species having GAP activity, in a preferred embodiment of the invention the entire purification procedure is carried out rapidly in the cold to reduce protease activity. In general, this temperature is in a range below 10° C., with a preferred temperature range being about 2°-8° C. Most preferred is a temperature of about 4° C.

Finally, it should be noted that while the preferred applications of the ion exchange materials described herein is in a column format, it will be appreciated that they may also be used in batch format as well.

GAP Assay

Several assays have recently been described to measure GAP activity. Trahey, M. and McCormick, F., *Science*, 238:542 (1987); Adari, et al., *Science*, 240:518 (1988). These references are herein incorporated in their entirety.

GAP may be assayed in vitro, and several different types of in vitro assays can be performed. The preferred assay involves measuring the presence of GDP resulting from the hydrolysis of GTP. This assay involves combining in an appropriate physiologically buffered aqueous solution empirically determined optimal amounts of normal cellular p21, and $\alpha$-$^{32}$P-GTP, plus GAP. The solution may also contain protease inhibitors and a reducing agent. Also, since cations greatly stimulate GAP activity they should be present in an effective amount. The preferred cation is magnesium chloride.

The reaction solution is incubated for various times and may be conducted at temperatures typically employed to perform enzymatic assays, preferably 10°-40° C., and more preferably at 37° C. At the appropriate times aliquots are removed and assayed for $\alpha$-$^{32}$P-GDP. This is readily accomplished by first separating p21 containing bound $\alpha$-$^{32}$P-GDP from the other reactants in the solution, particularly free $\alpha$-$^{32}$P-GTP. This can be achieved by immunoprecipitating p21 with antibodies directed thereto. Immune precipitation techniques and anti-p21 antibodies are known, and routinely employed by those skilled in the art. $\alpha$-$^{32}$P-GDT, is released from the immune precipitate preferably by dissolving the sample in a denaturing detergent at an elevated temperature, more preferably in 1% sodium dodecyl sulfate at 65° C. for five minutes, and chromatographing the mixture on a suitable thin layer chromatographic plate. The chromatography is preferably carried out on a PEI cellulose plate in 1M LiCl. $\alpha$-$^{32}$P-GDP is identified by its mobility relative to a known standard using suitable radiodetection techniques, preferably autoradiography.

An alternative assay for GAP activity is to substitute $\gamma$ labeled $^{32}$P-GTP for $\alpha$-labeled $^{32}$P-GTP in the above assay system, and assay for free $^{32}$P labeled phosphate using activated charcoal. This assay can be carried out as described by Tjian et al., *Cold Spring Harbor Symp. Quant. Biol.*, 44:103 (1980).

An additional assay does not involve immune precipitation. Rather an aliquot from a GAP assay reaction mixture described above can be directly subjected to PEI cellulose chromatography in 1M LiCl. This assay, however, is most useful for assaying solutions having substantially purified GAP.

Ras p21 Assay

One aspect of the instant invention is that the applicants have discovered a method whereby normal cellular p21 can be assayed. Although other assays present exist, for example, Western blotting using anti-p21 antibodies, the instant assay is complementary in nature, and facilitates the identification and characterization of tumors having abnormally elevated levels of normal p21. One of the key components in the assay is GAP, and it may be employed in one or more compositions utilized in different assay formats. Because GAP specifically stimulates normal cellular p21 GTPase activity, GAP can be used to assay for p21 in the presence of GTPases present in cell extracts.

Tumor cell extracts can be assayed for normal cellular p21 by adding GAP to a solution containing the cell extract, GTP, and the other reagents described in the preceding section, depending on the degree of GAP or p21 proteolyses and the need for cation stimulation of GAP activity. If p21 is present, there will be an enhancement in GTPase activity resulting from GAP stimulation. If p21 is not present, then the stimulation will not be apparent. It is important to note that not only is wild-type normal cellular ras p21 assayable by this method, but a variety of non-transforming mutants of normal ras p21 can also be assayed. These are shown by Adari, H., et al., above.

It is important to note that because most cells so far studied contain GAP, tumor cell extracts will likely contain endogenous GAP that may reduce or decrease the extent of GTPase stimulation resulting from GAP present in the reaction mixture. Thus, it may be desirable, even preferable, to partially purity p21 from tumor cell extracts before running the assay. p21 can be purified as described by Trahey, et al., *Mol. Cell. Biol.*, 7:541 (1987).

Identification of Anti-Cancer Therapeutics

A second application of the instant compositions described herein is the identification of anti-cancer therapeutics, particularly those that are effective against ras related tumors. Without wishing to be held to a particular theory regarding the role that GAP plays in tumorigenesis, applicants believe that the compositions and methods described below are efficacious in identifying such therapeutics because of an intracellular complex that is associated with tumorigenesis, and that compounds which prevent the formation of, or which cause its disassociation, can prevent tumors, or cause tumor regression. Applicants believe that in the normal cell, cell growth is regulated by down regulation of GTP by p21 such that GTP is converted constantly and rapidly to GDP. This conversion is assisted by GAP stimulation of GTP hydrolysis by p21. GAP interaction with p21 containing bound GTP is believed to be transient, and results in the facilitation of normal cell growth. In contrast, tumorigenesis is thought to result from binding of GAP to oncogenic p21 containing bound GTP. In this instance, GAP possibly because of the mutated state of p21, does not readily disassociate from p21/GTP. It is the formation of this complex, GAP/p21/GTP, that is thought to be responsible directly or indirectly for tumor genes. Thus, applicants have developed an assay which may be used to identify chemicals that prevent or disrupt the proposed interaction of GAP with p21/GTP, which in turn mimics the normal cellular p21/GTP complex which apparently does not have GAP bound for more than very transient times. Consequently, therapeutics which prevent GAP binding to normal cellular p21, as assayed by a reduction in GTPase activity should have anti-cancer activity.

Accordingly, chemicals can be identified that have anti-cancer activity by performing a GAP assay as described above in the presence of the suspected anti-cancer therapeutic. If the chemical reduces GAP stimulated GTPase activity, then it is expected to have anti-cancer activity.

It will be appreciated that there are to be expected multiple classes of such cancer therapeutics. The two most apparent classes are, first, immunoglobulins, or fragments derived therefrom that bind to GAP to effect GAP interaction with p21/GTP. The second class consists of small molecular weight compounds that bind to either p21 or GAP at their interactive sites. Thus, it will be appreciated that molecules which bind either to GAP, or to p21 are assayable by a reduction of GAP stimulated GTPase activity.

An additional class of cancer therapeutics which may be identified by the instant assay are those that bind to p21 at a site remote from where GAP and p21 interact which induces a conformational change in p21, thereby altering GAP binding to the molecule.

Having generally described the invention, examples of particular applications of the invention will be presented below. However, it will be understood by those skilled in the art that the examples are presented in the spirit of illustration only, and that they are not intended to limit the scope of the invention.

EXAMPLE I

Purification of GAP-Cation/Anion/Hydrophobic Chromatography

GAP was isolated from 300 g of human placentas by the following three-step chromatographic procedure. Placentas were obtained shortly after delivery, and kept on ice until they were processed. After it was determined by standard tests that the placentas were free of HIV antibodies, they were processed as follows. The initial step consisted of mechanically removing connective tissue, and ridding the placentas of excess blood by multiple soakings in phosphate buffered saline (PBS). The placentas were then fragmented by freezing the tissue at $-70°$ C., followed by placing the tissue in solution of PBS containing 5 mM EGTA, 100 $\mu$M PMSF and disrupting the tissue in a blender until a uniform, fine suspension was apparent. The suspension was centrifuged at $100,000 \times g$ to remove insoluble debris, the supernatant removed and the proteinaceous material therein precipitated with 40% ammonium sulfate. The ammonium sulfate was removed, and the precipitated proteins resuspended in PBS containing 0.1% NP40 and 100 $\mu$M PMSF. This solution was immediately dialyzed against 20 mM potassium phosphate, 1 mM $MgCl_2$, 5 mM EGTA, 0.1 mM DTT, 100 $\mu$M PMSF, pH 6.1 for six hours. This solution was then immediately chromatographed on a cation matrix, S-Sepharose (fast flow, obtainable from Pharmacia Corporation), preequilibrated in 20 mM potassium phosphate, 1 mM $MgCl_2$, 5 mM EGTA, 0.1 mM DTT, 100 $\mu$M PMSF, pH 6.1.

Proteins absorbed to the cation exchanger were eluted with a linear salt gradient containing 0–0.6M sodium chloride. Using the GAP assay described below, most of the GAP activity was shown to be present in two peaks, a major peak eluting at a sodium chloride concentration of 100–150 mM, and a minor peak eluting at a sodium chloride concentration of 220–300 mM. The major peak was dialyzed against 30 mM Tris-HCl, 1 mM magnesium chloride, 1 mM EGTA, 0.1 mM DTT, 100 $\mu$M PMSF, pH 8.5. The dialyzate was applied to a anion exchange column, TSK-DEAE-5-PW ($150 \times 21.5$ mm). The anion exchange matrix was treated with a linear salt gradient ranging from 0–0.6M sodium chloride to elute the adherent proteins. Most of the GAP activity eluted at a sodium chloride concentration of about 130 mM NaCl. Those fractions containing GAP activity were pooled, brought to 0.5M ammonium sulfate, and passed through a hydrophobic column, phenyl-TSK HPLC. Proteins were eluted from the hydrophobic column using a crisscross gradient consisting of increasing ethylene glycol 0–30%, and decreasing ammonium sulfate, 0.5–0M. The majority of GAP activity eluted at a concentration of 24% ethylene glycol and 0.1 molar ammonium sulfate. GAP activity assays, as performed below, correlated with a protein band of about 120,000 daltons, as revealed by sodium dodecyl sulfate polyacrylamide gel electrophoresis on 6% gels run under reducing conditions (FIGS. 1A and 1B).

EXAMPLE II

Purification of GAP-Cation/Anion/Cation Chromatography

A second preferred procedure was employed to purify GAP. Human placentas were again obtained shortly after delivery, and soaked in ice cold PBS, and homogenized and clarified as described in Example I. Ammonium sulfate was again added to the clarified homogenate to a final concentration of 40% to precipitate proteinaceous material. The ammonium sulfate solution was allowed to stand for one hour at 4° C. prior to recovering the precipitated proteinaceous material by centrifugation for 15 minutes at $10,000 \times g$. The pellet was resuspended in PBS containing 0.1% NP40 and 100 $\mu$M PMSF. This solution was dialyzed for six hours at 4° C. against 20 mM potassium phosphate, pH 6.1, containing 1 mM $MgCl_2$, 5 mM EGTA, 0.1 mM DTT, and 100 $\mu$M PMSF. Because GAP is susceptible to proteolysis, longer dialysis times are not desirable.

The GAP dialyzate was diluted three-fold with 4 mM potassium phosphate, pH 6.1, containing 0.02M $MgCl_2$, 1 mM EGTA, 0.1 mM DTT, and 100 $\mu$M PMSF to lower the conductivity of the solution to 1 millisiemens. This conductivity is compatible with application of the dialysate to a S-Sepharose cation exchange column. The dialysate was clarified by centrifugation at $10,000 \times g$ for 10 minutes, followed by a further clarification step consisting of filtration through a 0.45 μM filter, prior to adding the dialysate to the S-Sepharose column (fast-flow, Pharmacia). Most of the contaminating proteins passed through the S-Sepharose column, and the adsorbed proteins eluted with a 1.5 liter salt gradient consisting of 0–0.6M NaCl. Those fractions containing GAP activity were identified using the GAP assay described below.

As observed in the first example, GAP eluted from the cation exchange column in predominantly two major peaks. The first peak eluting over a sodium chloride concentration of 100–150 mM was pooled and dialyzed against 30 mM Tris-HCl buffer, pH 8.5, containing 1 mM EGTA, 1 mM $MgCl_2$, 0.1 mM DTT and 100 μM PMSF. The solution was dialyzed at 4° C., and clarified by filtration with a 0.45 μM filter. The filtrate was divided into equal halves, and each half purified using two consecutive anion exchange columns.

Figure 2:
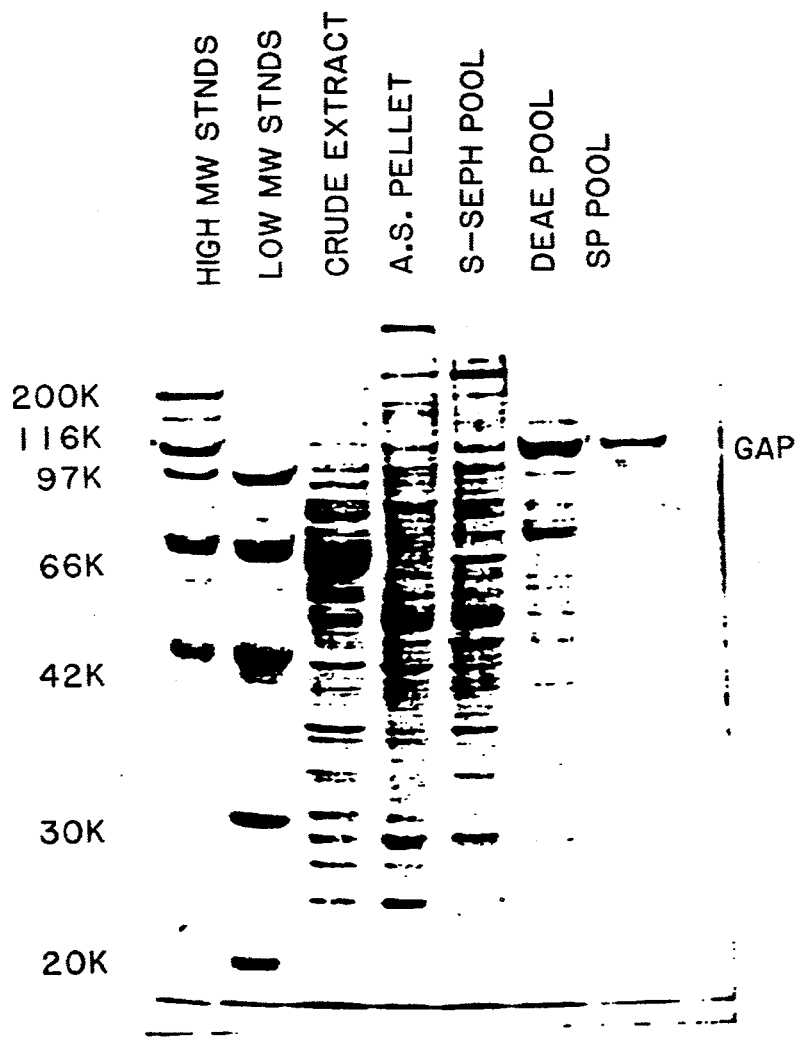
FIG. 2 shows the SDS gel profile of GAP purified by a three-step chromatographic scheme consisting of cation, and anion chromatography, followed by a second cation chromatographic step.

The two filtrates were separately loaded onto a TSK-DEAE-5-EW column having the dimensions 150×21.5 mm. The column was preequilibrated in the Tris-hydrochloride, pH 8.5 dialysis buffer described above. GAP was eluted from the column with a 60-minute 0–0.6M NaCl gradient with a flow rate of 3 ml/minute. The majority of the GAP activity from both filtrates eluted as a single peak at a sodium chloride concentration of about 130 mM. Sodium dodecyl sulfate, polyacrylamide gel electrophoretic analysis of the DEAE fractions showed that GAP was the major protein in the peak activity fractions. Fractions containing GAP from both purifications were pooled and diluted 5-fold into 2 mM potassium phosphate, pH 6.1, containing 0.1 mM EGTA, 10 μM DTT, 10 μM PMSF to lower the salt concentration to insure that the solution was chromatographically compatible with a second cation exchange chromatographic step, that is, chromatographed over a SP-TFK column. The pH of the solution was checked and adjusted to pH 6.1 with sodium acetate if necessary 3M pH 4.8. Both of the GAP fractions isolated from the DEAE columns were further purified separately over a cation column, TSK-SP-5-PW having dimensions of 75×7.5 mm. A solution containing 20 mM potassium phosphate, pH 6.1, containing 1 mM EGTA, 0.1 DTT, and 0.1 mM PMSF was passed through the column, followed by eluting GAP with a 45-minute, 0–0.6M sodium chloride gradient at 1 ml per minute. Those fractions containing GAP were identified using the assay described below and sodium dodecyl sulfate polyacrylamide gel electrophoresis. GAP activity corresponded to a protein having a molecular weight of about 116,000 daltons. Amino acid analysis was performed on the purified GAP to determine protein concentration. Starting with about 300 grams of human placenta, approximately 430 micrograms of purified GAP was obtained. FIG. 2 shows the SDS PAGE analysis of GAP at the various stages of purification described above.

EXAMPLE III

GAP Amino Acid Sequence

The protein having a molecular weight of 120,000 obtained by the purification method of Example I was electro-eluted from a 6% sodium dodecyl sulfate, polyacrylamide gel in 0.05 molar ammonia bicarbonate containing 0.1% sodium dodecyl sulfate. The procedure followed is described by Hunkapillar et al. The electro-eluted protein was fragmented for internal sequencing using lysyl endopeptidase (5% w/w, 18 hours at 40° C., WAKO). Peptides were fractionated by reverse-phase high performance liquid chromatography using a Brownlee Aquapore RP-300 cartridge (100×2.1 mm, Applied Biosystems). Peptides were eluted with an Acetonitrile gradient from 0–70% in 120 minutes (Buffer A, 0.1% trifluoroacetic acid (TFA) in H20; Buffer B, 0.085% TFA in 85% acetonitrile). Automated sequence analysis of the peptides was conducted on an Applied Biosystems 470A gas-phase sequencer as reported). A peptide characteristic of GAP has the following amino acid sequence: I M P E E Y S E F K.

EXAMPLE IV

GAP Assay

Approximately 0.8 micrograms of H-ras protein obtained as described by Trahey, et al., supra was bound to $\alpha$-$^{32}$P-GTP followed by precipitation of the complex with 13 micrograms of an anti-ras antibody, 157–181, that recognizes the carboxyl terminal end of the molecule. Specifically, 157–181 recognizes the carboxyl terminal residues at positions 157–181. Adari, et al., *Science*, 280:518 (1988). Next, 10 micrograms of sheep-anti-mouse IgG, and 10 microliters of protein A-Sepharose beads were added. As a control, the same reactants were combined except that rat IgG replaced 157–181, and goat anti-rat IgG replaced sheep anti-mouse IgG. The pellets were washed with 20 mM tris hydrochloride, pH 7.4, containing 20 mM sodium chloride, 1 mM magnesium chloride and 1 mM DTT and resuspended in the same solution. Four microliter aliquots of the immune complex were then mixed with 10 microliters of GAP, or, as a control, buffer without GAP. After 60 minutes incubation at room temperature the Sepharose beads were washed again, and the bound nucleotides analyzed using thin layer chromatography with 1M LiCl as the solvent. The thin layer plate was audioradiographed for one-two hours after which it was developed. The audioradiograph revealed that addition of sufficient GAP causes the near complete hydrolysis of GTP to GDP, whereas very little GTP hydrolysis occurs in the control lacking GAP. The assay detects GAP in a semi-quantitative, dose-dependent fashion. Quantitation can be improved by scraping the relevant regions of the plate and measuring cpm in GDP by use of a gamma counter. The immune precipitation controls having rat IgG substituted for the mouse antibodies revealed no GTP or GDP.

In addition to the above method, GAP can be preferably assayed as follows. Four μM normal cellular p21 was dissolved in a buffer containing 80 mM β-glycero-phosphate, 5 mM $MgCl_2$, 1 mM DTT, pH 7.5, plus 255 μM [$\alpha$-$^{32}$P] GTP (16 Ci/mmol), 4 mM ATP, and bovine serum albumin (2.5 mg/ml). The mixture was preincubated for 30 minutes at 37° C., followed by the addition of either a sample suspected of contained GAP, or an equal volume of buffer. After one hour at room temperature the monoclonal antibody Y13-259 in the presence of 0.5% NP40 was added in an amount sufficient to bind all the p21 present in the solution. Next, goat anti-Rat Ig-Protein A Sepharose was added to collect p21 bound to Y13-259, and the immune complex isolated and washed ten times in 20 mM Tris-HCl, pH 8.0, 100 mM NaCl, 5 mM $MgCl_2$, and 0.5% NP40. To determine the extent of GTP binding and hydrolysis during these steps a control was run consisting of adding 5 μg of p21 immediately before adding Y13-259.

Nucleotides were eluted from p21 with 1% SDS, 20 mM EDTA at 65° C. for five minutes and chromatographed on PEI Cellulose in 1M LiCl. GTP and GDP were visualized using standard autoradiographic techniques. The results showed that normal cellular p21 affects a nearly complete conversion of GTP to GDP when compared to mutant ras oncogenic proteins Asp 12 and Val 12 assayed similarly. Moreover, little or no GTP or GDP was detected in the control sample.

The assays described above are presented in more detail by Trahey and McCormick in *Science*, 238:542 (1987), and by Adari et al. in *Science*, 240:518 (1988). Both of these references are hereby incorporated by reference.

EXAMPLE V

Identification of Normal Cellular ras 21 in Tumor Samples

A variety of technical procedures can be employed using GAP to assay for the expression of normal cellular p21 in tumor tissues. One procedure may consist of isolating p21 by extraction techniques well known to those skilled in the art, Trahey et al. *Molecular and Cellular Biol.* 7:541 (1987), and combining the extract with a solid support matrix, preferably agarose beads that have bound anti-p21 antibodies. Alternatively, p21 may be assayed directly without purification. The antibodies should be selected so as to bind normal cellular p21 without affecting its intrinsic GTPase activity. Such antibodies as well as methods whereby they are bound to a solid support, are well known to those skilled in the art. Thus, p21 present in the tumor extract can be bound to anti-p21 antibody, which in turn is bound to agarose beads. The beads are then washed with a buffer compatible with performing the GTPase assay described in Example III, followed by the addition of an appropriate amount of $\alpha^{32}$-GTP, GAP, and the other reagents described in Example III to optimize the GTPase stimulation by GAP. This mixture is incubated at 37° C., and GTP hydrolysis measured by thin layer chromatography using 1 molar lithium chloride as the solvent.

Several controls should be run to insure that GAP-stimulated GTPase activity is indeed due to the presence of normal cellular p21. These controls are readily apparent to those skilled in the art, and include running in parallel in the assay a reaction mixture lacking normal cellular p21, as well as replacing the anti-p21 antibodies with antibodies that lack p21 specificity. Additional, it will be appreciated that the amount of normal cellular p21 in the tumor can be quantitated by running known amounts of normal cellular p21 in the assay, and constructing a standard curve wherein the increase in GAP stimulated GTPase activity is related to the amount of normal cellular p21.

It is worth noting that the contribution of endogenous GAP present in the tumor tissue extract to GAP stimulated GTPase activity measured n the assay is minimized by both purifying p21, as well as binding p21 to beads that are readily washed to remove any residual contaminating endogenous GAP prior to performing the assay.

EXAMPLE VI

Identification of Cancer Therapeutics

Molecules having anti-cancer activity can be identified by performing the GAP-stimulated GTPase assay as described in Example III in the presence of compounds suspected of having such activity. A reduction in GAP stimulated GTPase activity indicates that the compounds should have anti-tumor activity. It will be appreciated that water soluble compounds can be added directly to the assay mixture, whereas non-water soluble compounds may be dissolved in an organic solvent, and then added to the reaction mixture. The amount of organic solvent should not substantially interfere with the enzymatic reaction.

Having generally described the invention, it will be understood by those skilled in the art that there exists a wide range of equivalent materials and methods that can be substituted for those shown herein without effecting the spirit or scope of the invention. The scope of the invention should not be construed as being limited other than by the appended claims.

What is claimed is:

1. A isolated and substantially pure protein molecule comprising an apparent molecular weight of about 115,000–120,000 daltons as assessed by sodium dodecyl sulfate polyacrylamide gel electrophoresis run under reducing condition that simulate non-oncogenic ras p21 GTPase activity but does not substantially affect GTPase activity of oncogenic mutants.

2. A method of purifying a molecule having an apparent reduced molecular weight of about 115,000–120,000 daltons that simulates non-oncogenic ras p21 GTPase activity, but does not substantially affect GTPase activity of oncogenic mutants, from a solution containing the same, comprising the steps of:

contacting said solution with cation exchange chromatographic material for a time sufficient for said molecule to bind to said material;

forming a first eluate containing said molecule by eluting said molecule from said cation chromatographic material by contacting said chromatographic material with an aqueous salt solution;

identifying fractions in said first eluate having said molecular, and reducing the salt concentration present in said fractions to be compatible with anion exchange chromatography;

forming a second eluate by contacting said fractions of said first eluate containing said molecule with anion exchange chromatographic material for a time sufficient for said molecule to bind to said material, and eluting said molecule from said material anion exchange material with an aqueous salt solution;

forming a third eluate by contacting said second eluate with a second cation exchange chromatographic material for a time sufficient for said molecule to bind to said material, and eluting said material from said second cation exchange chromatographic material; and identifying fractions of said third eluate containing said molecule.

3. The method as described in claim 1 wherein said molecule is purified from human placenta.

4. The method as described in claim 1 wherein said purification is conducted in solutions containing one or more protease inhibitors at concentrations that effectively inhibit proteolysis of said molecule.

5. The method as described in claim 4 wherein said molecule is present in a solution comprising a reducing agent in an amount effective to preserve the activity of said molecule.

6. The method as described in claim 5 wherein said purification is conducted in solutions containing one or more metal ion chelators at concentrations that prevent substantial loss of activity of said molecule.

7. The method as described in claim 6 wherein said purification is conducted in solutions containing cations in an amount that substantially maintains the activity of said molecule.

8. The method as described in claim 7 wherein said cation is magnesium chloride.

9. The method as described in claim 1 wherein said solution contains about 1 mM magnesium chloride, 5 mM EGTA, 0.1 mM DTT, and 100 µM PMSF.

10. The method as described in claim 1 wherein said first cation exchange chromatographic material is S-Sepharose.

11. The method as described in claim 1 wherein said anion exchange chromatographic material is diethyl aminoethyl.

12. The method as described in claim 1 wherein said second cation chromatographic material comprises sulfopropyl functional groups.

13. The method as described in claim 10 wherein said second cation exchange material is TSK-SE-5-PW.

14. The method as described in claim 1 wherein a hydrophobic interaction chromatographic material is substituted for said second cation exchange material, and said second eluate from said anion exchange chromatographic material is made compatible with said hydrophobic interaction chromatographic material by increasing the ionic strength of said second eluate, and forming a third eluate by eluting said molecule from said hydrophobic interaction chromatographic material.

15. The method as described in claim 14 wherein said molecule is eluted from said hydrophobic interaction chromatographic material with an aqueous low salt solution, or an effective amount of a polyol.

16. The method as described in claim 14 wherein said hydrophobic interaction chromatographic material is under high pressure.

17. An isolated and substantially pure protein molecule as described in claim 1, wherein said non-oncogenic ras p21 GTPase activity is associated with H-ras.

18. An isolated and substantially pure protein molecule as described in claim 1, wherein said non-oncogenic ras p21 GTPase activity is associated with N-ras.

* * * * *